US005891723A

United States Patent [19]

Loughran, Jr. et al.

[11] Patent Number: 5,891,723
[45] Date of Patent: *Apr. 6, 1999

[54] LARGE GRANULAR LYMPHOCYTE LEUKEMIA ASSOCIATED VIRUS

[75] Inventors: Thomas P. Loughran, Jr., Cazenovia; Bernard J. Poiesz, Tully, both of N.Y.; Francis W. Ruscetti, New Market, Md.

[73] Assignees: The Research Foundation of State University of New York, Albany, N.Y.; The United States of America as represented by The Department of Health and Human Services, Washington, D.C.; Central New York Research Corporation, Syracuse, N.Y.

[*] Notice: The term of this patent shall not extend beyond the expiration date of Pat. No. 5,521,083.

[21] Appl. No.: 653,382

[22] Filed: May 24, 1996

Related U.S. Application Data

[63] Continuation of Ser. No. 242,680, May 13, 1994, Pat. No. 8,521,083.

[51] Int. Cl.[6] .............................. C12N 5/08; C12N 5/10; C12N 7/00
[52] U.S. Cl. ............................................ 435/366; 435/372
[58] Field of Search .............................. 435/235.1, 240.2, 435/366, 372

[56] References Cited

U.S. PATENT DOCUMENTS

| | | | |
|---|---|---|---|
| 4,804,746 | 2/1989 | Yoshida et al. | 530/387.9 |
| 5,077,194 | 12/1991 | Heeny et al. | 435/5 |
| 5,239,056 | 8/1993 | Portetellie et al. | 530/317 |
| 5,521,083 | 5/1996 | Loughran et al. | 435/235.1 |

FOREIGN PATENT DOCUMENTS

PCT/JP88/00-136  2/1987  Japan.

OTHER PUBLICATIONS

Fan, N., et al., "Infection of Peripheral Blood Mononuclear Cells and Cell Lines by Cell–Free Human T–Cell Lymphoma/Leukemia Virus Type I," *J. Clin. Microbiol.* 30(4):905–910 (1992).

Loughran, Jr., T.P., et al., "Detection of Human T–Cell Leukemia/Lymphoma Virus, Type II, in a Patient with Large Granular Lymphocyte Leukemia," *Blood* 80(5):1116–1119 (1992).

Loughran, Jr., T.P., "Clonal Diseases of Large Granular Lymphocytes," *Blood* 82(1):1–14 (1993).

*Primary Examiner*—David Guzo
*Attorney, Agent, or Firm*—Charles K. Sholtz; Gary R. Fabian; Peter J. Dehlinger

[57] ABSTRACT

A large granular lymphocyte (LGL) leukemia related virus has been isolated and characterized from patients having LGL leukemia. The virus appears to be related to the family of retroviruses including HTLV-I, HTLV-I and Bovine Leukemia Virus. Nucleic acid sequences of the virus are presented.

8 Claims, 7 Drawing Sheets

Fig. 1A

| Patient | R.A. | Serologic Reactivity | | Cambridge W.B. | | |
|---|---|---|---|---|---|---|
| | | HTLV-I ELISA | HTLV-II ELISA | env | gag | |
| 1 | - | - | - | | | p24 |
| 2 | + | - | - | p21e | p19 | p24 |
| 3 | - | - | - | p21e | | p24 |
| 4 | - | + | - | p21e | | p24 |
| 5 | + | - | - | | p19 | |
| 6 | + | - | - | | | p24 |
| 7 | - | + | - | p21e | | |
| 8 | + | - | - | p21e | | p24 |
| 9 | + | - | - | p21e | | |
| 10 | + | - | - | p12e | | p24 |
| 11 | - | - | - | | | p24 |
| 12 | - | - | - | | - | |
| 13 | - | - | - | | p19 | p24 |
| 14 | - | - | - | p21e | p19 | |
| 15 | - | + | + | | | p24 |
| 16 | + | - | - | | | p24 |
| 17 | + | - | - | | | p24 |
| 18 | - | + | + | | | p24 |
| 19 | + | - | - | p21e | p19 | p24 |
| 20 | - | - | - | | p19 | p24 |
| 21 | + | + | + | p21e | p19 | p24 |
| 22 | - | - | - | | | p24 |
| 23 | - | - | - | | | p24 |
| 24 | - | + | + | p21e gp46 | p19 | p24 |
| 25 | + | - | - | p21e | | p24 |
| 26 | + | - | - | | | p24 |
| 27 | - | - | - | p21e | p19 | p24 |
| 28 | - | - | - | | | |

Fig. 1B

| Patient | Serologic Reactivity Cambridge W.B. | | | | PCR Reactivity pol | pX |
|---|---|---|---|---|---|---|
| 1 | | | | | - | - |
| 2 | | | | | - | - |
| 3 | | | | | - | - |
| 4 | p42 | | | | - | - |
| 5 | | | | | - | - |
| 6 | | | | | - | - |
| 7 | p26 | p28 | p32 | p53 | - | - |
| 8 | p42 | | | | - | - |
| 9 | | | | | - | - |
| 10 | p42 | | | | - | - |
| 11 | p42 | p53 | | | - | - |
| 12 | | | | | - | - |
| 13 | p28 | p42 | | | - | - |
| 14 | p24 | p42 | p53 | | - | - |
| 15 | | | | | - | - |
| 16 | p38 | p46 | | | - | - |
| 17 | | | | | - | - |
| 18 | | | | | - | - |
| 19 | p26 | p32 | p42 | | - | - |
| 20 | p26 | p42 | p53 | | - | - |
| 21 | | | | | - | - |
| 22 | | | | | - | - |
| 23 | p53 | | | | - | - |
| 24 | | | | | + | + |
| 25 | | | | | - | - |
| 26 | | | | | - | - |
| 27 | p26 | | | | - | - |
| 28 | p26 | p42 | p53 | | - | - |

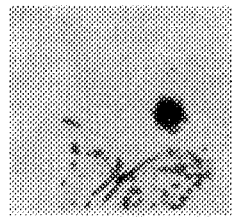 
Fig. 5A    Fig. 5B
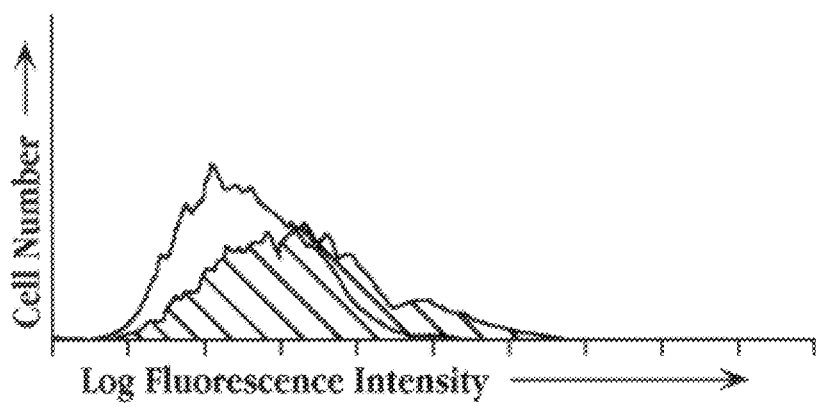
Fig. 6

```
GCCTGGTGTGCCCCCTCTGCGGGCCCCATGAGGGACTCGAAAGGATCGACACCACGCTCACCTGCG   70  Japanese BLV
...............................................A....................  70  Belgian BIV
......................................................................  70  PA. BIV
...............................A......................................  70  Patient 6
...............................A.................................T....  70  B-HOS
...............................A......................................  70  Patient 18
```

Fig. 7

```
AATGCTCTTACAAAGCCCATTCCGGCACTCTCCCGGACCGCCAGACCTTACGGCTATCCTAGCAACCTCCACATATCATTTGCCTAGATCTCAAAG  100  Lambdablv1
.............C...................................................A..T.................................  100  Pblv1
.........C..T.C...................................................A..T.................................  100  Pennblv
.........C......G.................................................A..T.................................  100  Patient 6
.........C........................................................C..A...T.........................TT.  100  Australian BLV
```

```
ATGCCCTTCTTCC  112  Lambdablv1
.............  112  Pblv1
.............  112  Pennblv
.............  112  Patient 6
.............  112  Australian BLV
```

Fig. 8

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
   ( A ) LENGTH: 22 base pairs
   ( B ) TYPE: nucleic acid
   ( C ) STRANDEDNESS: single
   ( D ) TOPOLOGY: linear ( i i ) MOLECULE TYPE: DNA ( i i i ) HYPOTHETICAL: NO ( v i ) ORIGINAL SOURCE:
   ( C ) INDIVIDUAL ISOLATE: SK142, BLV pX ( x i ) SEQUENCE DESCRIPTION: SEQ ID NO:1:

GTCCAATGAT GTCACCATCG AT                                                                      22

( 2 ) INFORMATION FOR SEQ ID NO:2:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( v i ) ORIGINAL SOURCE:
      ( C ) INDIVIDUAL ISOLATE: SK143, BLV, pX ( x i ) SEQUENCE DESCRIPTION: SEQ ID NO:2:

TCCAGTTGAT ACGGTGGGTC T                                                                       21

( 2 ) INFORMATION FOR SEQ ID NO:3:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( v i ) ORIGINAL SOURCE:
      ( C ) INDIVIDUAL ISOLATE: SK144, BLV, pX ( x i ) SEQUENCE DESCRIPTION: SEQ ID NO:3:

GAGCGACTCC AATTCGAAAC GATCGACACC                                                              30

( 2 ) INFORMATION FOR SEQ ID NO:4:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( v i ) ORIGINAL SOURCE:
      ( C ) INDIVIDUAL ISOLATE: SK139, BLV, pol ( x i ) SEQUENCE DESCRIPTION: SEQ ID NO:4:

TTTGTGCATG ACCTACGAGC TACA                                                                    24

( 2 ) INFORMATION FOR SEQ ID NO:5:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( v i ) ORIGINAL SOURCE:
  ( C ) INDIVIDUAL ISOLATE: SK140, BLV, pol ( x i ) SEQUENCE DESCRIPTION: SEQ ID NO:5:

AAGCGGTCTT CGACTGGAAT CT    22

( 2 ) INFORMATION FOR SEQ ID NO:6:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( v i ) ORIGINAL SOURCE:
  ( C ) INDIVIDUAL ISOLATE: SK141, BLV, pol ( x i ) SEQUENCE DESCRIPTION: SEQ ID NO:6:

TTTGAGATCT AGGCAAATGA TATGTGGAGG GTGCGT    36

( 2 ) INFORMATION FOR SEQ ID NO:7:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( v i ) ORIGINAL SOURCE:
  ( C ) INDIVIDUAL ISOLATE: HTLV II, pol, SK110

( x i ) SEQUENCE DESCRIPTION: SEQ ID NO:7:

CCATACAACC CCACCAGCTC AG    22

( 2 ) INFORMATION FOR SEQ ID NO:8:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( v i ) ORIGINAL SOURCE:
  ( C ) INDIVIDUAL ISOLATE: HTLV II, pol, SK111

( x i ) SEQUENCE DESCRIPTION: SEQ ID NO:8:

GTGGTGGATT TGCCATCGGG TTTT    24

( 2 ) INFORMATION FOR SEQ ID NO:9:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( v i ) ORIGINAL SOURCE:
  ( C ) INDIVIDUAL ISOLATE: HTLV II, pol, SK188 PROBE a ( x i ) SEQUENCE DESCRIPTION: SEQ ID NO:9:

TCATGAACCC CAGTGGTAAA        20

( 2 ) INFORMATION FOR SEQ ID NO:10:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( v i ) ORIGINAL SOURCE:
  ( C ) INDIVIDUAL ISOLATE: HTLV I, pol, SK112 PROBE b ( x i ) SEQUENCE DESCRIPTION: SEQ ID NO:10:

GTACTTTACT GACAAACCCG ACCTAC        26

( 2 ) INFORMATION FOR SEQ ID NO:11:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( v i ) ORIGINAL SOURCE:
  ( C ) INDIVIDUAL ISOLATE: HTLV II, pX, SK43

( x i ) SEQUENCE DESCRIPTION: SEQ ID NO:11:

CGGATACCCA GTCTACGTGT        20

( 2 ) INFORMATION FOR SEQ ID NO:12:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( v i ) ORIGINAL SOURCE:
  ( C ) INDIVIDUAL ISOLATE: HTLV II, pX, SK44

( x i ) SEQUENCE DESCRIPTION: SEQ ID NO:12:

GAGCCGATAA CGCGTCCATC G        21

( 2 ) INFORMATION FOR SEQ ID NO:13:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( v i ) ORIGINAL SOURCE:
    ( C ) INDIVIDUAL ISOLATE: HTLV II, pX, SK45 PROBE c ( x i ) SEQUENCE DESCRIPTION: SEQ ID NO:13:

ACGCCCTACT GGCCACCTGT CCAGAGCATC AGATCACCTG      40

( 2 ) INFORMATION FOR SEQ ID NO:14:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( v i ) ORIGINAL SOURCE:
    ( C ) INDIVIDUAL ISOLATE: HTLV II, gag p19, GE61

( x i ) SEQUENCE DESCRIPTION: SEQ ID NO:14:

GGGATTTGAA TTCCTCCATT C      21

( 2 ) INFORMATION FOR SEQ ID NO:15:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( v i ) ORIGINAL SOURCE:
    ( C ) INDIVIDUAL ISOLATE: HTLV II, gag p19, GE62

( x i ) SEQUENCE DESCRIPTION: SEQ ID NO:15:

GCTGCTGGAA GTCGAAATCG GAGGGCC      27

( 2 ) INFORMATION FOR SEQ ID NO:16:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( v i ) ORIGINAL SOURCE:
    ( C ) INDIVIDUAL ISOLATE: HTLV II, gag p19, GE, PROBE ( x i ) SEQUENCE DESCRIPTION: SEQ ID NO:16:

GCTATCAACC CACCACTGGC TTAACTTTCT CCAGGCTGC      39

( 2 ) INFORMATION FOR SEQ ID NO:17:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( v i ) ORIGINAL SOURCE:
    ( C ) INDIVIDUAL ISOLATE: HTLV I, gag p24, SG1

( x i ) SEQUENCE DESCRIPTION: SEQ ID NO:17:

CTGCAGTCAT GCATCCACAT GGTG    24

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: HTLV I, gag p24, SG2

( x i ) SEQUENCE DESCRIPTION: SEQ ID NO:18:

CTGCAGGAGG TCTTGGAGGT CTTT    24

( 2 ) INFORMATION FOR SEQ ID NO:19:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: HTLV I, gag p24, SG3, PROBE ( x i ) SEQUENCE DESCRIPTION: SEQ ID NO:19:

CCTCCTAACC ATCGCCCATG GCAAATGAAA GACCTACAGG    40

( 2 ) INFORMATION FOR SEQ ID NO:20:

( i ) SEQUENCE CHARACTERISTICS:
        ( A ) LENGTH: 70 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( v i ) ORIGINAL SOURCE:
        ( C ) INDIVIDUAL ISOLATE: JAPANESE BLV, pX ( x i ) SEQUENCE DESCRIPTION: SEQ ID NO:20:

GCCTGGTGCC CCCTCTGCGG GCCCCATGAG CGACTCCAAT TCGAAAGGAT CGACACCACG    60

CTCACCTGCG    70

( 2 ) INFORMATION FOR SEQ ID NO:21:

( i ) SEQUENCE CHARACTERISTICS:
        ( A ) LENGTH: 70 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( v i ) ORIGINAL SOURCE:
        ( C ) INDIVIDUAL ISOLATE: BELGIAN BLV, pX ( x i ) SEQUENCE DESCRIPTION: SEQ ID NO:21:

```
GCCTGGTGCC CCCTCTGCGG GCCCCATGAA CGACTCCAAT TCGAAAGGAT CGACACCACG    60

CTCACCTGCG                                                           70
```

( 2 ) INFORMATION FOR SEQ ID NO:22:

( i ) SEQUENCE CHARACTERISTICS:
        ( A ) LENGTH: 70 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( v i ) ORIGINAL SOURCE:
        ( C ) INDIVIDUAL ISOLATE: Patient 6, pX ( x i ) SEQUENCE DESCRIPTION: SEQ ID NO:22:

```
GCCTGGTGCC CCCTCTGCGG GCCCCATGAA CGACTCCAAT TCGAAAGGAT CGACACCACG    60

CTCACCTGCG                                                           70
```

( 2 ) INFORMATION FOR SEQ ID NO:23:

( i ) SEQUENCE CHARACTERISTICS:
        ( A ) LENGTH: 70 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( v i ) ORIGINAL SOURCE:
        ( C ) INDIVIDUAL ISOLATE: B-HOS, pX ( x i ) SEQUENCE DESCRIPTION: SEQ ID NO:23:

```
GCCTGGTGCC CCCTCTGCGG GCCCCATGAA CGACTCCAAT TCGAAAGGAT CGACACTACG    60

CTCACCTGCG                                                           70
```

( 2 ) INFORMATION FOR SEQ ID NO:24:

( i ) SEQUENCE CHARACTERISTICS:
        ( A ) LENGTH: 70 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( v i ) ORIGINAL SOURCE:

(C) INDIVIDUAL ISOLATE: Patient 18, pX (x i) SEQUENCE DESCRIPTION: SEQ ID NO:24:

| | | | | | |
|---|---|---|---|---|---|
|GCCTGGTGCC|CCCTCTGCGG|GCCCCATGAA|CGACTCCAAT|TCGAAAGGAT|CGACACCACG|60|
|CTCACCTGCG| | | | |70|

(2) INFORMATION FOR SEQ ID NO:25:

(i) SEQUENCE CHARACTERISTICS:
        (A) LENGTH: 112 base pairs
        (B) TYPE: nucleic acid
        (C) STRANDEDNESS: double
        (D) TOPOLOGY: linear (i i) MOLECULE TYPE: cDNA (i i i) HYPOTHETICAL: NO (v i) ORIGINAL SOURCE:
        (C) INDIVIDUAL ISOLATE: LAMBDABLV, JAPANESE BLV, pol (x i) SEQUENCE DESCRIPTION: SEQ ID NO:25:

| | | | | | |
|---|---|---|---|---|---|
|AATGCTCTTA|CAAAGCCCAT|TCCGGCACTC|TCTCCCGGAC|CGCCAGACCT|TACCGCTATC|60|
|CCTACGCACC|CTCCACATAT|CATTTGCCTA|GATCTCAAAG|ATGCCTTCTT|CC|112|

(2) INFORMATION FOR SEQ ID NO:26:

(i) SEQUENCE CHARACTERISTICS:
        (A) LENGTH: 112 base pairs
        (B) TYPE: nucleic acid
        (C) STRANDEDNESS: double
        (D) TOPOLOGY: linear (i i) MOLECULE TYPE: cDNA (i i i) HYPOTHETICAL: NO (v i) ORIGINAL SOURCE:
        (C) INDIVIDUAL ISOLATE: PBLV1, BELGIAN BLV, pol (x i) SEQUENCE DESCRIPTION: SEQ ID NO:26:

| | | | | | |
|---|---|---|---|---|---|
|AATGCTCTTA|CAAAGCCCAT|CCCGGCACTC|TCCCCCGGAC|CGCCAGACCT|TACCGCTATC|60|
|CCTACACACC|TTCCACATAT|CATTTGCCTA|GATCTCAAAG|ATGCCTTCTT|CC|112|

(2) INFORMATION FOR SEQ ID NO:27:

(i) SEQUENCE CHARACTERISTICS:
        (A) LENGTH: 112 base pairs
        (B) TYPE: nucleic acid
        (C) STRANDEDNESS: double
        (D) TOPOLOGY: linear (i i) MOLECULE TYPE: cDNA (i i i) HYPOTHETICAL: NO (v i) ORIGINAL SOURCE:
        (C) INDIVIDUAL ISOLATE: Patient 6, pol (x i) SEQUENCE DESCRIPTION: SEQ ID NO:27:

| | | | | | |
|---|---|---|---|---|---|
|AATGCTCTTA|CAAAGCCCAT|CCCGGCGCTC|TCCCCCGGAC|CGCCAGACCT|TACCGCTATC|60|
|CCTACACACC|TTCCACATAT|CATTTGCCTA|GATCTCAAAG|ATGCCTTCTT|CC|112|

(2) INFORMATION FOR SEQ ID NO:28:

(i) SEQUENCE CHARACTERISTICS:
        (A) LENGTH: 112 base pairs
        (B) TYPE: nucleic acid (C) STRANDEDNESS: double
(D) TOPOLOGY: linear (ii) MOLECULE TYPE: cDNA (iii) HYPOTHETICAL: NO (vi) ORIGINAL SOURCE:
(C) INDIVIDUAL ISOLATE: Pennblv, Japanese BLV, pol (xi) SEQUENCE DESCRIPTION: SEQ ID NO:28:

AATGCTCTTA CAAAGCCCAT CCCGGCACTT TCCCCCGGAC CGCCAGACCT TACCGCTATC     60
CCTACACACC TTCCACATAT TATTTGCCTA GATCTCAAAG ATGCCTTCTT CC             112

(2) INFORMATION FOR SEQ ID NO:29:

(i) SEQUENCE CHARACTERISTICS:
(A) LENGTH: 112 base pairs
(B) TYPE: nucleic acid
(C) STRANDEDNESS: double
(D) TOPOLOGY: linear (ii) MOLECULE TYPE: cDNA (iii) HYPOTHETICAL: NO (vi) ORIGINAL SOURCE:
(C) INDIVIDUAL ISOLATE: Australian BLV, Patient 18, pol (xi) SEQUENCE DESCRIPTION: SEQ ID NO:29:

AATGCTCTTA CAAAGCCCAT CCCGGCACTC TCCCCCGGAC CGCCAGACCT TACCGCTATC     60
CCCACACACC TTCCACATAT CATTTGTTTA GATCTCAAAG ATGCCTTCTT CC             112

LARGE GRANULAR LYMPHOCYTE LEUKEMIA ASSOCIATED VIRUS

This is a continuation of application Ser. No. 08/242,680, filed May 13, 1994, now U.S. Pat. No. 5,521,083.

This invention was made with Government support under grant CA 54552 awarded by the National Cancer Institute, grant NO1 HB 67021 awarded by the National Heart, Lung, and Blood Institute. Accordingly, the government has certain rights in this invention.

FIELD OF THE INVENTION

The present invention relates to nucleic acid, antigen, and antibody compositions of large granular lymphocyte (LGL) leukemia related virus.

REFERENCES

Anagnostopoulos, I., et al., *Am. J. Pathol.* 137(6):1317 (1990).
Anderson, D. W., et al., *Blood* 74:2585 (1989).
Ausubel, F. M., et al., *Current Protocols in Molecular Biology*, John Wiley and Sons, Inc., Media Pa.
Beames, et al., *Biotechniques* 11:378 (1991).
Bennett, J. M., et al., *J. Clin. Pathol.* 42:567 (1989).
Bennett, J. M., et al., *Cancer Res.* 50:2212 (1990).
Brouet, J.-C., et al., *Lancet* ii:890 (1975).
Clapham, P., et al., *Science* 22:1125 (1983).
Erlich, G. D., et al., *Blood* 74:1658 (1989).
Fan, N., et al., *J. Clin. Microbiol.* 30(4):905–910 (1992).
Hadlock, K. G., et al., *Blood* 79:2789 (1992).
Hall, W. W., et al., *Science* 253:317 (1991).
Harlow, E., et al., *Antibodies: A Laboratory Manual*, Chapter 10, pg. 402, Cold Spring Harbor Press (1988).
Hitzeman, R. A., et al., U.S. Pat. No. 4,775,622, issued Oct. 4, 1988.
Hjelle, B., et al., *Blood* 81:1641 (1993).
Ijichi, S., et al., *J. Exp. Med.* 176:293 (1992).
Kalyanaraman, V. S., et al., *Science* 218:571 (1993).
Lal, R. B., et al., *J. Clin. Microbol.* 29:2253 (1991).
Lal, R. B., et al., *Blood* 80:544 (1992).
LeDeist, F., et al., *Cancer* 67:2610 (1991).
Lee, H., et al., *Science* 244:471 (1989).
Levitt, L. J., et al., *J. Clin. Invest.* 81:538 (1988).
Lillehoj, E. P., et al., *J. Clin. Microbiol.* 28:2653 (1990).
Lipka, J. J., et al., *J. Infect. Dis.* 165:268 (1992).
Loughran, T. P., Jr., et al., *Ann. Intern. Med.* 102:169 (1985).
Loughran, T. P., Jr., et al., *Blood* 69:72 (1987).
Loughran, T. P., Jr., and Starkebaum, G., *Medicine* 66:397 (1987).
Loughran, T. P., Jr., and Hammond, W. P., *J. Exp. Med.* 164:2089 (1988).
Loughran, T. P., Jr., et al., *Arthritis Rheum.* 31:31 (1988a).
Loughran, T. P., Jr., et al., *Blood* 71:822 (1988b).
Loughran, T. P., et al., *Blood* 72:613 (1988c).
Loughran, T. P., Jr., et al., *Blood* 80:1116 (1992).
Loughran, T. P., Jr., *Blood* 82:1 (1993).
Maniatis, T., et al. *Molecular Cloning: A Laboratory Manual*, Cold Spring Harbor Laboratory (1982).
Miyoshi, I., et al., *Nature* 294:770 (1981).
Mullis, K. B., U.S. Pat. No. 4,683,202, issued Jul. 28, 1987.
Mullis, K. B., et al., U.S. Pat. No. 4,683,195, issued Jul. 28, 1987.
Morgan, J. G., et al., *Nucleic Acids Res.* 20(19):5173–5179 (1992).
Newland, A. C., et al., *Br. J. Haematol.* 58:433 (1984).
Oeda, K., et al., U.S. Pat. No. 4,766,068, issued Aug. 23, 1988.
Pandolfi, F., et al., *Lancet* ii:1527 (1987).
Poiesz, B. J., et al., *Proc. Natl. Acad. Sci. USA* 77:7415 (1980).
Poiesz, B. J., et al., *Medical Virol.* 9:42–75 (1990).
Reilly, P. R., et al., *Baculovirus Expression Vectors: A Laboratory Manual* (1992).
Reyes, G., et al., Molecular and Cellular Probes 5:473–481 (1991).
Robert-Guroff, M., et al., *J. Exp. Med.* 154:1957 (1981).
Rosenblatt, J. D., et al., *N. Engl. J. Med.* 315:372 (1986).
Rosenblatt, J. D., et al., *Blood* 71:363 (1988).
Rutter, W. J., et al., U.S. Pat. No. 4,769,238, issued Sep. 6, 1988.
Sagata, N., et al., *Proc. Natl. Acad. Sci. USA* 82:677 (1985).
Sambrook, J., et al., In *Molecular Cloning: A Laboratory Manual*, Cold Spring Harbor Laboratory Press, Vol. 2 (1989).
Scharf, S. J., et al., *Science* 233:1076 (1986).
Seelig, R., et al., *Leukemia* 7(11):1886–1887 (1993).
Semenzato, G., et al., *Cancer* 60:2971 (1987).
Sherman, et al., *J. Clin. Microbiol.* 30:185–191 (1992).
Smith. D. B., et al, *Gene,* 67:31 (1988).
Starkebaum, G., et al., *Lancet* i:596 (1987).
Williams, A. E., et al., *Science* 240:643 (1988).
Yoshikai, Y., et al., *Nature* 312:521 (1984).

BACKGROUND OF THE INVENTION

The French-British-American (FAB) Cooperative Group has classified chronic T-lymphoid leukemias into four subgroups: (i) T-cell or LGL leukemia, (ii) T-prolymphocytic leukemia (T-PLL), (iii) adult T-cell leukemia/lymphoma, and (iv) Sezary's syndrome (Bennett, et al., 1989).

Chronic lymphocytic leukemia (CLL) of T-cell origin was first identified in 1975. In many patients the abnormal cells were large granular lymphocytes (LGL) (Brouet, et al., 1975). The MIC Cooperative Group reviewed the FAB classification in 1990 and proposed that Large Granular Lymphocyte (LGL) leukemia should replace T-CLL as the preferable terminology (Bennett, et al., 1990).

Clonal disorders of LGL may arise from either natural killer cells or T cells; it has been suggested that these diseases be designated, NK-and T-LGL leukemia, respectively (Loughran, 1993). T-LGL leukemia is characterized by clonal proliferation of CD3+ LGL with are usually also CD8+, CD16+, and CD57+ (Loughran, 1993; Loughran, et al., 1985; Loughran and Starkebaum, 1987; Newland, et al., 1984; Semenzato, et al., 1987).

Clinical manifestations of T-LGL leukemia include rheumatoid arthritis, splenomegaly, and hematologic abnormalities such as chronic or cyclic neutropenic, autoimmune thrombocytopenia, and pure red cell aplasia (Loughran, 1993; Loughran, et al., 1985; Loughran and Starkebaum, 1987; Newland, et al., 1984; Semenzato, et al., 1987; Loughran and Hammond, 1988).

SUMMARY OF THE INVENTION

The present invention pertains to the characterization and isolation of a newly discovered etiologic agent—LGL leukemia-associated retrovirus. Specifically, portions of LGL leukemia-associated retrovirus genome are presented.

Portions of the sequences derived from LGL leukemia-associated retrovirus are effective as probes to isolate variants of the virus which occur naturally, or to determine the presence of virus in samples. These polynucleotide sequences also make available polypeptide sequences of LGL leukemia-associated retrovirus antigens encoded within LGL leukemia-associated retrovirus genome(s). Further, these polynucleotides allow the production of polypeptides that are useful as reagents in diagnostic tests and/or as components of vaccines, or as standards.

Both polyclonal and monoclonal antibodies directed against LGL leukemia-associated retrovirus epitopes contained within the polypeptide sequences are also useful as therapeutic agents, for diagnostic tests, for the isolation of the LGL leukemia-associated retrovirus agent from which these identified sequences have been derived. Included in the invention are purified preparations of polyclonal antibodies directed against a LGL leukemia-associated retrovirus epitope; and monoclonal antibodies directed against a LGL leukemia-associated retrovirus antigen.

Another aspect of the invention is a method for producing antibodies to LGL leukemia-associated retrovirus, comprising administering to a subject a separate immunogenic polypeptide containing a LGL leukemia-associated retrovirus epitope in an adequate amount to present an immune response.

Further, isolation of other portions of the LGL leukemia-associated retrovirus genome can be accomplished utilizing probes derived from the identified LGL leukemia-associated retrovirus sequences (e.g., SEQ ID NO:22, SEQ ID NO:23, SEQ ID NO:24, and SEQ ID NO:27). These further sequences provide additional probes and polypeptides useful in the diagnosis and/or treatment of both prophylactic and therapeutic LGL leukemia-associated retrovirus.

With respect to polynucleotides, the present invention includes the following embodiments: a purified LGL leukemia-associated retrovirus; a recombinant LGL leukemia-associated retrovirus; a recombinant polynucleotide making up a sequence derived from a LGL leukemia-associated retrovirus or from LGL leukemia-associated retrovirus cDNA; a recombinant polynucleotide encoding an epitope of LGL leukemia-associated retrovirus; a recombinant vector including any of the above recombinant polynucleotides; and host cells transformed with any of these vectors. Further embodiments of the present invention include polynucleotide probes and primers for LGL leukemia-associated retrovirus. Probes may be used, for example, in hybridization-based assays. Primers can be used, for example, in amplification reactions.

Also included in the invention are a method for the detection of LGL leukemia-associated retrovirus nucleic acids in samples comprising reacting nucleic acids of the sample with a probe for a LGL leukemia-associated retrovirus polynucleotide, under conditions allowing the creation of a polynucleotide duplex between the probe and the LGL leukemia-associated retrovirus nucleic acid from the sample; as well as detecting a polynucleotide duplex containing the probe.

Other aspects of the invention include the following: recombinant expression systems incorporating an open reading frame (ORF) of DNA derived from a LGL leukemia-associated retrovirus or from LGL leukemia-associated retrovirus cDNA, where the ORF is linked operably to a control sequence compatible with a desired host; cells transformed with such recombinant expression systems; and polypeptides produced by the transformed cell (i.e., recombinantly produced polypeptides). Further, the invention includes the following: a technique for the production of a polypeptide which contains a LGL leukemia-associated retrovirus, which includes incubating host cells which are transformed with an expression vector, containing a sequence encoding a polypeptide which contains a LGL leukemia-associated retrovirus epitope, under conditions which allow expression of said polypeptide; and a polypeptide which contains a LGL leukemia-associated retrovirus which has been produced by this method.

Another aspect of this invention is a tissue culture grown cell, infected with a LGL leukemia-associated retrovirus.

Still further embodiments of the present invention are purified LGL leukemia-associated retrovirus particles, preparation of polypeptides from the purified LGL leukemia-associated retrovirus particles; purified LGL leukemia-associated retrovirus polypeptides; and purified polypeptides comprising epitopes immunologically identifiable with an epitope contained in a LGL leukemia-associated retrovirus.

The following embodiments of the invention are related to LGL leukemia-associated retrovirus polypeptides: recombinant polypeptides consisting of sequences derived from an LGL leukemia-associated retrovirus genome or from LGL leukemia-associated retrovirus cDNAs; recombinant polypeptides comprising LGL leukemia-associated retrovirus-specific epitopes; and fusion polypeptides including LGL leukemia-associated retrovirus protein coding sequences.

The present invention also contemplates kits for use in a variety of diagnostic and screening methods. For example, investigating samples for the presence of polynucleotides derived from LGL leukemia-associated retrovirus—e.g., a polynucleotide probe including a nucleotide sequence from LGL leukemia-associated retrovirus of approximately 8 or more nucleotides; analyzing samples for the presence of antibodies directed against a LGL leukemia-associated retrovirus antigen—a polypeptide which contains a LGL leukemia-associated retrovirus epitope present in the LGL leukemia-associated retrovirus antigen.

Still other aspects of the invention include a polypeptide comprised of a LGL leukemia-associated retrovirus epitope, which is attached to a solid substrate; and an antibody to a LGL leukemia-associated retrovirus epitope, which is attached to a solid substrate.

The invention also includes immunoassays, including an immunoassay for detecting a LGL leukemia-associated retrovirus, comprising the incubation of a sample which is suspected of including a LGL leukemia-associated retrovirus with a probe antibody directed against the LGL leukemia-associated retrovirus, to be detected under conditions allowing the formation of an antigen-antibody complex; and for detecting an antigen-antibody complex which contains the probe antibody. The invention also includes, an immunoassay for the detection of antibodies which are directed against a LGL leukemia-associated retrovirus antigen comprising the incubation of a sample suspected of containing LGL leukemia-associated retrovirus with a probe polypeptide including an epitope of the LGL leukemia-associated retrovirus, under conditions that allow the formation of an antibody-antigen complex; and distinguishing the antibody-antigen complex which contains the probe antigen.

Vaccines for treatment of LGL leukemia-associated retrovirus infection comprising an immunogenic peptide containing a LGL leukemia-associated retrovirus, or an inactivated preparation of LGL leukemia-associated retrovirus are also part of the invention.

These and other objects and features of the invention will be more fully appreciated when the following detailed description of the invention is read in conjunction with the accompanying drawings.

BRIEF DESCRIPTION OF THE FIGURES

FIGS. 1A and 1B show the results of HTLV-I/II antibody and polymerase chain reaction reactivity in samples from LGL-leukemia patients. In the figures, R.A.=rheumatoid arthritis.

FIGS. 5A and 5B present computer-scanned images of electron micrographs of viral particles of the present invention.

FIG. 6 present the results of flow cytometry analysis of the staining of B-HOS cells with HTLV-I/II anti-p19 monoclonal antibody.

FIG. 7 presents sequence comparisons between several Bovine Leukemia Virus pX gene isolates (SEQ ID NOS:20–24) and LGL leukemia-associated retrovirus isolates of the present invention.

FIG. 8 presents sequence comparisons between several Bovine Leukemia Virus pol gene isolates (SEQ ID NOS:25–29) and LGL leukemia-associated retrovirus isolates of the present invention.

DETAILED DESCRIPTION OF THE INVENTION

I. ETIOLOGY OF LARGE GRANULAR LYMPHOCYTE LEUKEMIA

Figure 2A:
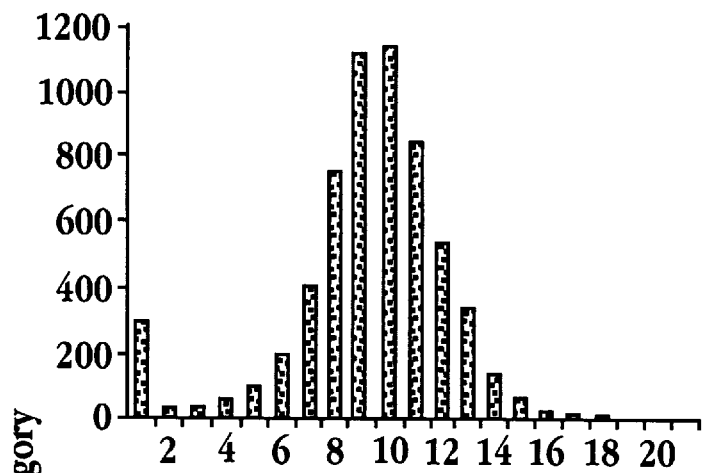
FIGS. 2A, 2B and 2C show histograms of natural logarithm-transformed signal/cutoff values for antibodies to HTLV-I/II from LGL leukemia-patients' sera.

Retroviral infection has been linked to the development of other clonal T-cell diseases (Poiesz, et al., 1980). Standard criteria established by the Public Health Service for defining Human T-Cell Leukemia/Lymphoma Virus (HTLV) I and II seropositivity are antibodies to p24 gag protein and either gp46 or gp68 env proteins in sera which had previously tested positive in a whole virus ELISA (Anderson, et al., 1989).

Serologic assays to confirm and differentiate HTLV-I and HTLV-II have been hindered by loss of env antigenicity during processing for Western blot assays and the high degree of antigenic similarity between HTLV-I and HTLV-II. Consequently, little is known about the role of HTLV-I in disease pathogenesis, although it is recognized that intravenous drug users are often infected with HTLV-II rather than HTLV-I (Lee, et al., 1989; Erlich, et al., 1989).

In 1987, it was reported that 6 of 12 patients with Large Granular Lymphocyte (LGL) leukemia had antibodies to HTLV-I/II gag proteins (Starkebaum, et al., 1987). A similar pattern of seroreactivity was observed in 7 of 27 European patients with LGL leukemia (Pandolfi, et al., 1987). Recently, HTLV-II was cloned and sequenced from the bone marrow of a patient with LGL leukemia (Loughran, et al., 1992). In addition, the patient's serum had antibodies that were specific for HTLV-II. HTLV-II has also been associated with a lymphoproliferative disorder of clonal CD8+ cells (Rosenblatt, et al., 1988); furthermore, HTLV-II preferentially infects CD8+ cells in vivo (Ijichi, et al., 1992).

Together with the observation that sera from HTLV-II-infected individuals often have only indeterminate gag reactivity in conventional Western blot assays (Lee, et al., 1989), these findings raised the possibility that seroreactivity in T-LGL leukemia patients may be directed against HTLV-II rather than HTLV-I. Experiments performed in support of the present invention, however, demonstrate that patients with LGL leukemia are not infected with prototypical HTLV-I or HTLV-II.

Twenty-eight patients were involved in the studies described herein. The patients had clonal proliferations of LGL as determined by T-cell receptor β-gene rearrangement (27 patients) (Loughran, et al., 1988b) and/or cytogenetic (2 patients) (Loughran, et. al., 1985) studies.

Sera from these twenty eight LGL leukemia patients were screened for HTLV-I and HTLV-II antibodies using several ELISA assays (Example 1). It has been shown that sera from some HTLV-II-infected individuals test negative in an HTLV-I whole virus ELISA (Lee, et al., 1989; Erlich, et al., 1989). For these reasons, all patients' sera were tested using new serologic assays which, by incorporating recombinant proteins or peptides, can confirm and distinguish HTLV-I from HTLV-II infection (Lillehoj, et al., 1990; Lipka, et al., 1992). Serum from only one patient tested positive in these assays; that patient was infected with HTLV-II, as determined previously (Loughran, et al., 1992). Serum from another patient appeared positive for HTLV-I showing reactivity to gag protein p24 and recombinant HTLV-I gp46 env protein. However, that serum was negative in the whole virus assay and did not react to recombinant p21e env protein.

The results of the serological analysis are presented in FIGS. 1A and 1B and summarized in Table 1. A much higher percentage of these sera tested positive in these assays compared to results from normal blood donors (6/28=21.4% versus 0.17% normal donors) (Williams, et al., 1988).

Figure 2B:
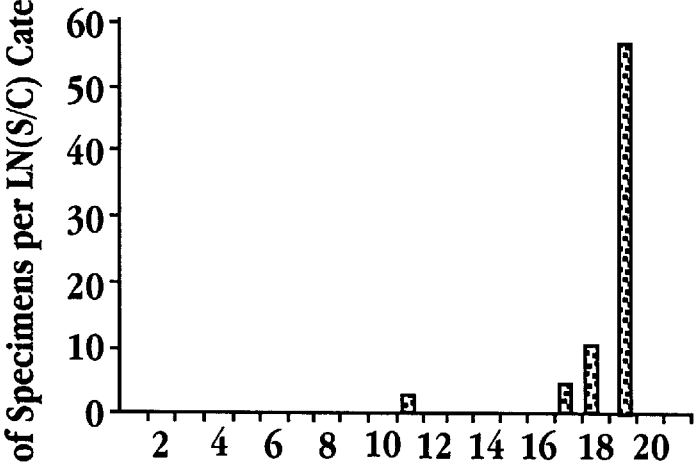
Figure 2C:
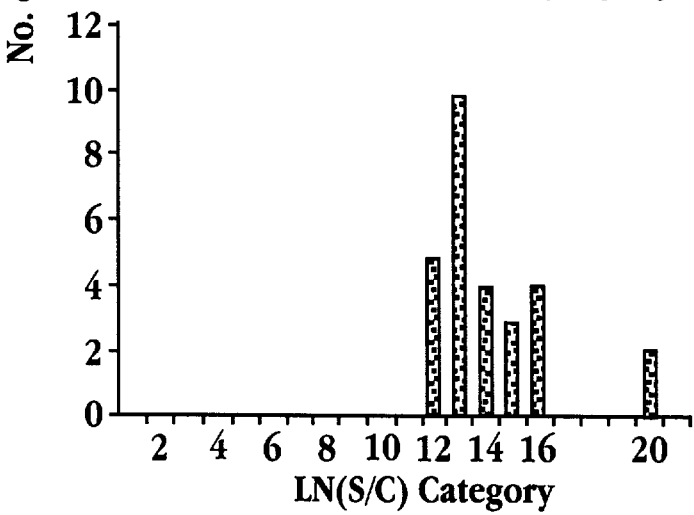

To further evaluate these serological results, control sera were collected from 6,080 volunteer blood donors, from 400 patients with other leukemias, and from 72 patients documented to be HTLV-I positive by nucleic acid studies. FIGS. 2A, 2B and 2C show histograms of natural logarithm-transformed signal/cutoff values for antibodies to HTLV-I/II. (Example 1). The ELISA negative sera from T-LGL leukemia patients clustered near the positive cutoff value—a distribution which was significantly different than that of sera from normal blood donors as demonstrated by two statistical methods: Fisher's exact T-test and Chi square analyses. Both of these analyses suggested that the distribution of HTLV-I/II ELISA reactivity in LGL leukemia sera was significantly different than results obtained in normal sera.

All but one of the present 28 sera tested negative for HTLV pX and pol gene sequences (Example 3, FIGS. 1A and 1B). Further, protein blots of HTLV-I/II specific antigens were screened with the 28 sera, described above, to detect any immunoreactivity (Western blot analysis, Example 2). Sera from 89% of our patients (25 of 28) had HTLV-I/II-specific antibodies to one retroviral gene product by Western blot.

Although this pattern of reactivity is considered indeterminate by conventional criteria, the specific proteins recognized by these sera differed from other populations. For example, in serologically indeterminate donors that also test HTLV-negative by polymerase chain reaction diagnostics, antibody to gag protein p19 alone is the most common finding (68–84%); reactivity to gag protein p24 is uncommon (10–16%) (Hadlock, et al., 1992; Lal, et al., 1992).

In contrast, in the 25 HTLV-PCR-negative, indeterminate sera (FIGS. 1A and 1B) only 1 patient had antibody to p19 alone, 21 of these patients (84%) had reactivity to gag protein p24. Because of difficulty in showing reactivity with retroviral envelope proteins in standard Western blots, new assays have incorporated recombinant HTLV-I envelope protein, p21e. Sera with antibodies to either HTLV-I or HTLV-II react equally to p21e (Lillehoj, et al., 1990). Using the "CAMBRIDGE WESTERN BLOT ASSAY" (Materials and Methods), 48% of indeterminate sera from our patients were reactive with env protein, p21e and 40% had reactivity to both gag protein p24 and env protein p21e (FIG. 1). Only 8.5% and 2.9%, respectively, of 379 indeterminate sera from HTLV PCR-negative armed forces' blood donors had antibodies to these proteins using the same assay (Lal, et al., 1992).

The indeterminate HTLV-I/II serological reactivity data presented above suggest the association of an HTLV-I/II related retrovirus with LGL leukemia. An alternative explanation for the antibody reactivity described above would be non-specific protein interaction due to immune complexes or rheumatoid factor, which occur commonly in patients with T-LGL leukemia (Loughran, 1993). However, serum from only 1% of patients with autoimmune diseases had reactivity to gag and to env p21e in this assay ("CAMBRIDGE," Lillehoj, et al., 1990). Furthermore, sera from some patients in this study which were positive for env p21e were negative for immune complexes and rheumatoid factor.

II. FAMILIAL OCCURRENCE OF LGL LEUKEMIA

Experiments performed in support of the present invention demonstrate the familial occurrence of LGL leukemia in a mother and her son. Serologic studies for HTLV-I/II were negative in the mother but showed reactivity to gag proteins p19, p24, and p28 in the son.

The results presented in Example 4 demonstrate the familial occurrence of LGL leukemia. This data confirm a previous observation of LeDeist and colleagues in which LGL leukemia occurred in two siblings (LeDeist, et al., 1991).

Experiments performed in support of the present invention indicate that serum from the son was indeterminate for HTLV-I/HTLV-II, reacting only with gag proteins p19, p24 and p28 (Example 4). Since HTLV-II from a patient with LGL leukemia was recently cloned and sequenced (Loughran, et al., 1992), determination as to whether the indeterminate reactivity was directed against HTLV-II proteins was sought.

Patient serum did not react to recombinant env protein HTLV-I p21e, which was found to have equal reactivity to HTLV-I or HTLV-II positive sera (Lillehoj, et al., 1990). Furthermore, no reactivity to HTLV-I or HTLV-II using a synthetic peptide based-ELISA which was shown to have 100% to 96% sensitivity in detecting HTLV-I and HTLV-II respectively was found (Lal, et al., 1991) (Example 4).

Also, pX or pol sequences shared by HTLV-I/II or HTLV-I could not be detected (Example 4). PCR assays directed at regions of serologic reactivity (gag p19 and p24) were also negative in each patient.

These results further suggest that a retrovirus associated with familial cases of LGL leukemia is not prototypical HTLV-I or HTLV-II.

III. IDENTIFICATION OF AN LGL LEUKEMIA-ASSOCIATED RETROVIRUS

Experiments performed in support of the present invention suggest the association of a non-prototypical HTLV I/II-like retrovirus associated with LGL-leukemia. Transmission of an infective retrovirus from a patient with LGL leukemia to a human osteosarcoma (HOS) cell line has been demonstrated (Example 5). Splenic mononuclear cells were isolated from Patient 6 and grown as an IL-2 dependent cell line (Loughran, et al., 1988c). The splenic cell line was co-cultured with the HOS cell line. The HOS cell line was previously known to be able to be productively infected with HTLV-I/II (Clapham, et al., 1983). The cell line resulting from the splenic/HOS cell co-culture was named B-HOS.

Reverse transcriptase (RT) assays were performed at various intervals of cocultivation. There was no evidence of reverse transcriptase activity in control HOS supernatants. Further, RT levels were only minimally elevated in direct assays of LGL leukemia cell line supernatants.

However, RT activity was demonstrated in supernatants of B-HOS co-cultivated cell lines. Passage of B-HOS cells with 5-Iodo-2'deoxyuridine (IdUr) resulted in re-induction of reverse transcriptase activity (Example 5, Table 4). Levels of reverse transcriptase activity observed in B-HOS supernatants were comparable to those obtained from supernatants of a known HTLV-I producer cell line.

Further evidence for retroviral protein expression was obtained using commercially available monoclonal antibodies (Mab's) that are immunoreactive with HTLV-I/II gag proteins p19 and p24 (Example 5). B-HOS cell cultures were screened for proteins immunoreactive with the monoclonal antibodies. In time-point samples where RT activity was low, no cytoplasmic expression of HTLV-I/II gag proteins p19 or p24 was observed. However, the flow cytometry data presented in FIG. 6 demonstrate that there was an induction of cytoplasmic p19. Further, cytoplasmic p24 expression was induced in the B-HOS cells after treatment with IdUr (Example 5, Table 5).

Further evidence of an LGL leukemia-associated retroviral agent was obtained as follows. Supernatants from B-HOS cell lines were clarified and subjected to sucrose gradient analysis. Viral particles were purified from cell culture supernatants by double banding using sucrose gradient centrifugation (Example 5). Reverse transcriptase assays were performed on aliquots from each fraction. The reverse transcriptase activity peaked in two areas of the gradient, at densities of 1.19 to 1.21 g/ml and 1.10 g/ml. These activity peaks correspond to density fractions typical for retroviral particles.

Further, B-HOS cells were prepared for electron microscopic examination. Viral particles were visualized. Representative photographs of viral particles are shown in FIGS. 5A and 5B. Mature extracellular viral particles are approximately 100 nm in diameter. The particles have an electron-dense, centrally located nucleoid and are surrounded by an outer membrane. The outer membrane is separated from the nucleoid by an electron-lucent area.

The results presented above strongly support a non-prototypical HTLV-I/II retroviral infection associated with LGL leukemia. In order to characterize this new infectious agent, genomic DNA was isolated from the PBMC of LGL-leukemia patients and from B-HOS cells. Amplification primers were selected based on conserved sequences from the pX and pol gene coding sequences from Bovine Leukemia Virus (Example 6). The sequences of the amplified pX products are presented in FIG. 7 (Patient 6, SEQ ID NO:22; B-HOS, SEQ ID NO:23; Patient 18, SEQ ID NO:24). The sequence of an amplified pol product from the Patient 6 nucleic acid source is presented in FIG. 8 (SEQ ID NO:27). The sequences demonstrate a high homology to a number of isolates of Bovine Leukemia Virus (SEQ ID NOS: 20–24 in FIG. 7 and SEQ ID NOS: 25–29 in FIG. 8).

The data presented above support the identification and partial isolation of a human LGL leukemia-associated retrovirus.

IV. FURTHER CHARACTERIZATION OF LGL LEUKEMIA-ASSOCIATED RETROVIRUS

A. CLONING AND CHARACTERIZATION OF THE LGL LEUKEMIA-ASSOCIATED RETROVIRUS

Further LGL leukemia-associated retroviral sequences can be obtained as, for example, described above for SEQ ID NO:22 and SEQ ID NO:27. Further primers based on BLV sequences can be utilized potentially with inosine substitutions or limited degeneracy to allow for less specificity of primer to target hybridization.

Alternatively, the DNA fragments SEQ ID NO:22–SEQ ID NO:24 and SEQ ID NO:27 can be employed as probes in hybridization experiments to identify overlapping LGL leukemia-associated retrovirus sequences, and these in turn can be further used as probes to identify a set of contiguous clones. The generation of sets of contiguous clones allows the elucidation of the sequence of a given LGL leukemia-associated retrovirus agent's genome.

The following illustrates several approaches for the use of cloned insert-derived DNA to identify clones carrying other LGL leukemia-associated retrovirus sequences. The nucleotide sequences SEQ ID NO:22–SEQ ID NO:24 and SEQ ID NO:27 can be produced (e.g., by amplification or physical isolation from clones containing the sequences) and labeled with a detection moiety. These sequences are then used as hybridization probes against cDNA or DNA libraries established in lambda gt11 and gt10, respectively. The libraries are produced from patient PBMC nucleic acids by standard methods. The representation of low abundance sequences can be improved by, for example, hybridization selection (Morgan, et al., 1992) or amplification (Reyes, et al., 1991).

Inserts of overlapping clones identified by hybridization are then isolated by EcoRI digestion of the lambda gt10 clone, followed by electrophoretic fractionation and electroelution. Such isolated inserts can be treated with DNase I to generate random fragments and the resulting digested fragments are inserted into lambda gt11 phage vectors for immunoscreening with patient sera to yield immunoreactive regions.

Specific subfragments of any clone may be isolated by polymerase chain reaction or after cleavage with restriction endonucleases. These fragments can be used as radiolabelled probes against the libraries generated in lambda gt10. In particular, the 5' and 3' terminal sequences of the clone inserts are useful as probes to identify additional clones. In addition, the clone inserts can be used to screen other libraries, for example, sequences derived from one patient can be used to screen libraries generated from nucleic acids obtained from a second patient (e.g., patients 6 and 18).

Further, the sequences provided by the 5' end of cloned inserts are useful as sequence specific primers in first-strand cDNA synthesis reactions (Maniatis et al.; Scharf et al.). For example, cDNA and DNA libraries can be hybridized with a primer specific for SEQ ID NO:22–SEQ ID NO:24 or SEQ ID NO:27. These primer/template complexes are used for first strand synthesis. The second-strand of the new cDNA can be primed using random primers (e.g., random nucleotide hexamer primers; cDNA Synthesis Kit, Boehringer-Mannheim Biochemical, Indianapolis, Ind.) or primers derived from other BLV sequences (true or degenerate primers).

The above procedures identify or produce DNA/cDNA molecules corresponding to nucleic acid regions that are adjacent to the known LGL leukemia-associated retrovirus sequences. These newly isolated sequences can in turn be used to identify further flanking sequences, and so on, to identify the sequences composing the entire genome for a given LGL leukemia-associated retrovirus agent.

After new LGL leukemia-associated retrovirus sequences are isolated, the polynucleotides can be cloned and immunoscreened to identify specific sequences encoding LGL leukemia-associated retrovirus antigens. cDNA and DNA libraries are prepared from infected sera in an expression vector (e.g., lambda gt11). cDNA and DNA sequences are selected for the expression of polypeptides immunoreactive with LGL leukemia-associated retrovirus infected sera.

cDNA libraries are typically generated using random primers in reverse transcription reactions with RNA extracted from pelleted sera as starting material. DNA libraries were generated by protease K treatment and SDS lysis of pelleted sera, followed by the addition of Klenow fragment of DNA polymerase and random primers to the nucleic acid. Resulting fragments are cloned into a suitable vector, for example, lambda gt11, for expression and screening of peptide antigens, and the lambda gt10 vector, for hybridization screening.

Lambda gt11 particularly useful as an expression vector in that it contains a unique EcoRI insertion site 53 base pairs upstream of the translation termination codon of the beta-galactosidase gene. Accordingly, inserted sequences with reading frames continuous with the beta-galactosidase coding sequences are expressed as a beta-galactosidase fusion proteins. Such fusion proteins contain the N-terminal portion of the beta-galactosidase gene product, the heterologous peptide, and optionally the C-terminal region of the beta-galactosidase peptide (the C-terminal portion being expressed when the heterologous peptide coding sequence does not contain a translation termination codon). Phage containing a heterologous insert produces an inactive beta-galactosidase enzyme, phage with inserts are typically identified using a beta-galactosidase colored-substrate reaction.

First round screening is typically performed using the same sera that was used to generate the phage library, or, alternately, a closely related sera. Alternatively, other sera believed to be infected with LGL leukemia-associated retrovirus can be used.

Recombinant proteins identified by this approach provide candidates for polypeptides which can serve as substrates in diagnostic tests. Further, the nucleic acid coding sequences identified by this approach serve as useful hybridization probes for the identification of further LGL leukemia-associated retrovirus coding sequences.

Immunopositive clones are typically plaque-purified and their immunoreactivity retested. Also, the immunoreactivity of the clones with normal human sera is also tested. Clones are also examined for the "exogenous" nature of the cloned insert sequence. This basic test establishes that the cloned fragment does not represent a portion of the human or other known (e.g. bacterial) genomes.

The clone inserts are isolated by EcoRI digestion following polymerase chain reaction amplification. The inserts are purified, radiolabelled and used as hybridization probes against membrane bound control DNAs, for example, normal human DNA and bacterial DNA.

Antigen-encoding DNA fragment can be subcloned. The subcloned insert can then be fragmented by partial DNase I digestion to generate random fragments or by specific restriction endonuclease digestion to produce specific subfragments. The resulting DNA fragments can be inserted into the lambda gt11 vector and subjected to immunoscreening in order to provide an epitope map of the cloned insert.

B. RECOMBINANT PRODUCTION OF LGL LEUKEMIA-ASSOCIATED RETROVIRUS POLYNUCLEOTIDES AND POLYPEPTIDES

The present invention includes methods of recombinantly producing LGL leukemia-associated retrovirus polynucleotides and polypeptides. For recombinant production of polynucleotides, any of a number of cloning vectors and suitable hosts can be used (e.g., "TA" cloning vectors, Example 6). Isolated LGL leukemia-associated retrovirus polynucleotides are inserted into a cloning vector, the vector transformed into a suitable host, propagated, and the amplified vector isolated. The LGL leukemia-associated retrovirus polynucleotide can then be excised from the vector by restriction endonuclease digestion and purified by standard methods (Ausubel, et al.; Sambrook, et al.).

Typically, for recombinant production of polypeptides, a recombinant expression system containing an open reading frame (ORF) having a polynucleotide sequence which encodes a LGL leukemia-associated retrovirus polypeptide, where the vector is designed to express the ORF in the host, is introduced into suitable host cells. The host is then cultured under conditions resulting in the expression of the ORF sequence. Examples of polynucleotide coding sequences are SEQ ID NO:22–SEQ ID NO:24 and SEQ ID NO:27.

Numerous vectors and their corresponding hosts are useful in the practice of this method of the invention, including, lambda gt11 phage vector and *E. coli* cells. Recombinant LGL leukemia-associated retrovirus polypeptides are produced, for example, using bacterial, yeast and insect cell expression systems.

Typical yeast vectors that may be used in the practice of the present invention include, but are not limited to the following: vectors with regulatable expression (Hitzeman, et al.; Rutter, et al.; Oeda, et al.). The host for yeast transformation is typically *Saccharomyces cerevisiae*, however, other yeast suitable for transformation can be used as well (e.g., *Schizosaccharomyces pombe*).

Further, DNA encoding a LGL leukemia-associated retrovirus polypeptide can be cloned into any number of commercially available vectors to generate expression of the polypeptide in the appropriate host system. These systems include the above described bacterial and yeast expression systems as well as the following: pGEX (bacterial; Smith, et al, 1988; baculovirus expression (Reilly, et al.; Beames, et al.; Clontech, Palo Alto Calif.); and expression in mammalian cells (Clontech, Palo Alto Calif.; Gibco-BRL, Gaithersburg Md.).

Recombinant polypeptides may be expressed as fusion proteins or as native proteins. A number of features can be engineered into the expression vectors, such as leader sequences which promote the secretion of the expressed sequences into culture medium. The recombinantly produced polypeptides are typically isolated from lysed cells or culture media.

Purification of recombinantly produced proteins is carried out by methods known in the art, for example, size fractionation, salt fractionation, ion exchange chromatography, and affinity chromatography (solid support available from Pharmacia, Piscataway N.J.). Immunoaffinity chromatography can be employed using antibodies (see below). Protein preparations can also be concentrated by, for example, filtration (Amicon, Danvers, Mass.).

C. ANTI-LGL LEUKEMIA-ASSOCIATED VIRUS ANTIGEN ANTIBODIES

In another aspect, the invention includes antibodies specific against the recombinant antigens of the present invention. To prepare antibodies, a host animal, such as a rabbit, is immunized with the purified antigen or fused protein antigen. Host serum or plasma is collected following an appropriate time interval, and this serum is tested for antibodies specific against the antigen (e.g., ELISA or Western Blots; Harlow, et al.; Ausubel, et al.).

The gamma globulin fraction or the IgG antibodies of immunized animals can be obtained, for example, by use of saturated ammonium sulfate or DEAE Sephadex, or other techniques known to those skilled in the art for producing polyclonal antibodies. Fusion proteins can be isolated by affinity chromatography (e.g., an amylose affinity column for maltose-binding protein fusions; pMAL vectors and reagents, New England Biolabs, Beverly, Mass.).

Alternatively, purified antigens or fused antigen polypeptides can be used to producing monoclonal antibodies. Typically, the spleen or lymphocytes from an immunized animal are removed. These cells are then immortalized or used to prepare hybridomas by methods known to those skilled in the art (Harlow, et al.).

Antibodies secreted by the immortalized cells are screened to determine the clones that secrete antibodies of the desired specificity, for example, using the Western blot methods.

D. LGL LEUKEMIA-ASSOCIATED RETROVIRUS PARTICLES

LGL leukemia-associated retrovirus particles may be isolated from, for example, infected sera or cultured infected cells (Example 6, from B-HOS cells). Methods for the isolation of viral particles include techniques based on size fractionation (i.e., density centrifugation, precipitation, ultracentrifugation), use of anionic and/or cationic exchange materials, separation on the basis of hydrophilic properties, and affinity chromatography.

During the isolation procedure the LGL leukemia-associated retrovirus agents can be identified using anti-LGL leukemia-associated retrovirus antibodies of the present invention or by using hybridization probes.

Antibodies directed against LGL leukemia-associated retroviral agents can be used in purification of viral particles through immunoaffinity chromatography (Harlow, et al.; Pierce). Antibodies directed against LGL leukemia-associated retrovirus polypeptides or fusion polypeptides are fixed to solid supports in such a manner that the antibodies maintain their immunoselectivity. To accomplish such attachment of antibodies to solid support bifunctional coupling agents (Pierce; Pharmacia) containing spacer groups are frequently used to retain accessibility of the antigen binding site of the antibody.

LGL leukemia-associated retroviral particles can be further characterized by standard procedures including immunofluorescence microscopy, electron microscopy, Western blot analysis of proteins composing the particles, infection studies in animal and/or cell systems utilizing the partially purified particles, and sedimentation characteristics. Results of preliminary electron microscopic analysis shown in FIGS. 5A and 5B. These figures show retroviral-like particles present in B-HOS cell cultures—co-cultures of splenic cells from Patient 6 and HOS cells.

The LGL leukemia-associated retrovirus particles can be disrupted to obtain viral genomes. Disruption of the particles can be achieved by, for example, treatment with detergents in the presence of chelating agents. The genomic nucleic acid can then be further characterized. Characterization may include analysis of DNase and RNase sensitivity. The strandedness and conformation (i.e., circular) of the genome can be determined by techniques known in the art, including visualization by electron microscopy and sedimentation characteristics.

The isolated genomes also make it possible to sequence the entire genome whether it is segmented or not, and whether it is an RNA or DNA genome (using, for example RT-PCR, chromosome walking techniques, or PCR which utilizes primers from adjacent cloned sequences). Determination of the entire sequence of a LGL leukemia-associated retrovirus agent allows genomic organization studies and the comparison of the LGL leukemia-associated retrovirus sequences to the coding and regulatory sequences of known viral agents.

V. UTILITY

A. IMMUNOASSAYS FOR LGL LEUKEMIA-ASSOCIATED RETROVIRAL AGENTS

One utility for the antigens obtained by the methods of the present invention is the use of such antigens as diagnostic agents for LGL leukemia-associated retrovirus antibodies present in infected sera. The antigens of the present invention can be used singly, or in combination with each other, in order to detect single or multiple retroviral agents. For example, antigens immunoreactive with a LGL leukemia-associated retrovirus polypeptide may be combined in a blood diagnostic assay with antigens from other known retroviruses, such as, HTLV-I, HTLV-II, Hepatitis C Virus (HCV) and Human Immunodeficiency Virus (HIV).

In one diagnostic configuration, test serum is reacted with a solid phase reagent having a surface-bound antigen obtained by the methods of the present invention. After binding anti-LGL leukemia-associated retrovirus antibody to the reagent, unbound serum components are removed by washing. The reagent is reacted with reporter-labeled anti-human antibody to bind reporter to the reagent in proportion to the amount of bound anti-LGL leukemia-associated retrovirus antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric or colorimetric substrate (Sigma, Rockford Ill.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group.

In a second diagnostic configuration, known as a homogeneous assay, antibody binding to a solid support produces some change in the reaction medium which can be directly detected in the medium. Known general types of homogeneous assays proposed heretofore include (a) spin-labeled reporters, where antibody binding to the antigen is detected by a change in reported mobility (broadening of the spin splitting peaks), (b) fluorescent reporters, where binding is detected by a change in fluorescence efficiency, (c) enzyme reporters, where antibody binding effects enzyme/substrate interactions, and (d) liposome-bound reporters, where binding leads to liposome lysis and release of encapsulated reporter. The adaptation of these methods to the protein antigen of the present invention follows conventional methods for preparing homogeneous assay reagents.

In each of the assays described above, the assay method involves reacting the serum from a test individual with the protein antigen and examining the antigen for the presence of bound antibody. The examining may involve attaching a labeled anti-human antibody to the antibody being examined (for example from acute, chronic or convalescent phase) and measuring the amount of reporter bound to the solid support, as in the first method, or may involve observing the effect of antibody binding on a homogeneous assay reagent, as in the second method.

Also forming part of the invention is an assay system or kit for carrying out the assay method just described. The kit generally includes a support with surface-bound LGL leukemia-associated retrovirus antigen (e.g., the recombinantly produced antigens described above), and a reporter-labeled anti-human antibody for detecting surface-bound anti-LGL leukemia-associated retrovirus antibody.

A third diagnostic configuration involves use of anti-LGL leukemia-associated retrovirus antibodies capable of detecting LGL leukemia-associated retrovirus specific antigens. LGL leukemia-associated retrovirus antigens may be detected, for example, using an antigen capture assay where LGL leukemia-associated retrovirus antigens present in candidate serum samples are reacted with a LGL leukemia-associated retrovirus specific monoclonal or polyclonal antibody.

In this assay method, the antibody is bound to a solid substrate and binding of the antigen is then detected by a second, different labelled anti-LGL leukemia-associated retrovirus antibody. Antibodies can be prepared, utilizing the peptides of the present invention, by standard methods. Antibodies that are substantially free of serum proteins which may affect reactivity can be generated (e.g., affinity purification; Harlow, et al.).

B. HYBRIDIZATION ASSAYS FOR LGL LEUKEMIA-ASSOCIATED RETROVIRUS AGENTS.

One utility for the nucleic acid sequences obtained by the methods of the present invention is their use as diagnostic agents for LGL leukemia-associated retrovirus agent sequences present in infected sera. Primers and/or probes derived from the coding sequences of the present invention, e.g., SEQ ID NO:22–SEQ ID NO:24 and SEQ ID NO:27, can be used singly, or in combination with each other, in order to detect LGL leukemia-associated retrovirus infection.

In one diagnostic configuration, test serum is reacted under PCR or RT-PCR conditions using primers derived from LGL leukemia-associated retrovirus sequences. The presence of a LGL leukemia-associated retrovirus agent, in the serum used in the amplification reaction, can be detected by specific amplification of the sequences targeted by the primers.

Alternatively, probes can be derived from the LGL leukemia-associated retrovirus sequences of the present invention. These probes can then be labeled and used as hybridization probes against nucleic acids obtained from test serum or tissue samples. The probes can be labeled using a variety of reporter molecules and detected accordingly: for example, radioactive isotopic labelling and chemiluminescent detection reporter systems (Tropix, Bedford, Mass.).

Also forming part of the invention is assay systems or kits for carrying out the amplification/hybridization assay methods just described. Such kits generally include either specific primers for use in amplification reactions or hybridization probes.

C. THERAPEUTIC USES

LGL leukemia-associated retrovirus antigens of the present invention can be used in vaccine preparation.

Further, antibodies generated against the polypeptide antigens of the present invention can be used for passive immunotherapy. The anti-LGL leukemia-associated retrovirus antibodies of the invention can be used as a means of enhancing an anti LGL leukemia-associated retrovirus immune response since antibody-virus complexes are recognized by macrophages. The antibodies can be administered in amounts similar to those used for other therapeutic administrations of antibody.

For example, pooled gamma globulin is administered at 0.02–0.1 ml/lb body weight during the early incubation of other viral diseases such as rabies, measles and hepatitis B to interfere with viral entry into cells.

Antibodies reactive with LGL leukemia-associated retrovirus antigens can be passively administered alone or in conjunction with another anti-viral agent to a host infected with a LGL leukemia-associated retrovirus agent to enhance the immune response and/or the effectiveness of an antiviral drug.

The following examples illustrate, but in no way are intended to limit the present invention.

MATERIALS AND METHODS

A. GENERAL

E. coli DNA polymerase I (Klenow fragment) was obtained from Boehringer Mannheim Biochemicals (Indianapolis, Ind.). T4 DNA ligase and T4 DNA polymerase were obtained from New England Biolabs (Beverly, Mass.); Nitrocellulose filters were obtained from Schleicher and Schuell (Keene, N.H.). Restriction enzymes were obtained from a variety of manufacturer's and used following their instructions.

Synthetic oligonucleotide linkers and primers were prepared using commercially available automated oligonucleotide synthesizers. Alternatively, custom designed synthetic oligonucleotides may be purchased, for example, from Synthetic Genetics (San Diego, Calif.). cDNA synthesis kit and random priming labeling kits were obtained from Boehringer-Mannheim Biochemical (BMB, Indianapolis, Ind.).

Standard molecular biology and cloning techniques were performed essentially as previously described in Ausubel, et al., Sambrook, et al., and Maniatis, et al.

Common manipulations involved in polyclonal and monoclonal antibody work, including antibody purification from sera, were performed by standard procedures (Harlow, et al.). Pierce or Promega (Madison, Wis.) were sources of many antibody reagents.

B. PATIENTS

Twenty-eight patients were involved in the studies presented below. All the patients had clonal proliferations of LGL as determined by T-cell receptor β-gene rearrangement (27 patients) (Loughran, et al., 1988b) and/or cytogenetic (2 patients) (Loughran, et al., 1985) studies. The phenotype of leukemic LGL was CD3+, CD8+, CD57+, and usually also CD16+. LGL counts ranged from 680 to 17,290/μl (Loughran and Starkebaum, 1987). Twelve patients had rheumatoid arthritis. Familial occurrence of LGL leukemia was noted for patients 12 (mother) and 13 (son)—see below.

Control sera were collected from 6,080 volunteer blood donors, from 400 patients with other leukemias (including both acute and chronic myeloid (n=100) and lymphoid (n=300), and from 72 patients documented to be HTLV-I positive by nucleic acid studies.

C. ANTIBODY STUDIES

These assays included a HTLV-I enzyme-linked immunosorbent assay (ELISA) (Cellular Products, Buffalo, N.Y.) and an HTLV-II ELISA, performed as previously described (Loughran, et al., 1992). A modified recombinant HTLV-I/II Western blot kit (Cambridge Biotech, Cambridge, Mass.) was used according to the manufacturer's instructions, except that diaminobenzidine was used as the detection substrate (Harlow, et al., 1988). Alternatively, sera were studied using a synthetic peptide-based HTLV-I/II ELISA ("SELECT-HTLV", Coulter).

To further discriminate HTLV-I from HTLV-II infection, another modified recombinant HTLV-I/II Western blot assay (HTLV blot 2.3, Diagnostic Biotechnology, Ltd., Singapore) was used according to the manufacturer's instructions.

D. DNA ANALYSES

DNA from peripheral blood mononuclear cells was enzymatically amplified using the polymerase chain reaction (PCR; Mullis; Mullis, et al.) with the thermostable DNA polymerase Taq in a Perkin-Elmer Cetus Thermal Cycler (Norwalk, Conn.) for 45 cycles, essentially as previously described (Erlich, et al., 1989; Loughran, et al., 1992).

Many of the following primers and probes for HTLV-I and II have been previously described (Poiesz, et al., 1990).

Primers and probes are as follows: primer pair 1 HT II POL (4735–4756)+/HT II POL (4920–4897)–(SEQ ID NO:7 and SEQ ID NO:8, respectively); probe a HT II POL (4880–4899)+detector moiety ("+d") (SEQ ID NO:9); and probe b HT I POL (4825–4850)+d (SEQ ID NO:10); primer pair 2 HT II pX (7248–7267)+/HT II pX (7406–7386)–(SEQ ID NO:11 and SEQ ID NO:12, respectively); probe c HT II px (7337–7376)+d (SEQ ID NO:13).

Primer pairs 1 and 2 amplify pol and pX gene sequences, respectively, which are common to HTLV-I and HTLV-II. Probe a specifically detects the HTLV-II pol sequence, whereas probe b specifically detects the HTLV-I pol sequence; probe c detects either HTLV-I or HTLV-II pX sequences amplified by primer pair 2 (Erlich, et al., 1989).

For the familial study described below, DNA amplified by PCR was assayed for pX and pol gene sequences shared by HTLV-I and HTLV-II, as well as for HTLV-I-specific gag p24 (primers SEQ ID NO:17, and SEQ ID NO:18; probe, SEQ ID NO:19) and HTLV-II-specific gag p19 (primers SEQ ID NO:14, and SEQ ID NO:15; probe, SEQ ID NO:16), using the liquid hybridization format (Erlich, et al., 1989).

EXAMPLES

Example 1

SEROLOGICAL RESULTS

A. LGL LEUKEMIA PATIENT ELISA

Sera from the twenty eight LGL leukemia patients were screened for HTLV-I and HTLV-II antibodies using several ELISA assays (Materials and Methods). The serological results are presented in FIGS. 1A and 1B and summarized in Table 1.

TABLE 1

SUMMARY OF HTLV-I/II ANTIBODY REACTIVITY IN LGL LEUKEMIA

| HTLV-I/II Protein | Reactivity | Reactive/Tested (%) |
| --- | --- | --- |
| gag | any gag | 26/28 (93) |
|  | p19 only | 1/28 (4) |
|  | p24 | 23/28 (82) |
| env | gp46 | 2/28 (7) |
|  | p21e | 13/28 (46) |
| gag + env | p24 + gp46 | 2/28 (7) |
|  | p24 + p21e | 11/28 (39) |
|  | other gag + p21e | 1/28 (4) |

Sera from 6 patients (21%) were positive in an HTLV-I and/or HTLV-II whole virus ELISA. Sera from an additional 6 patients had ELISA reactivity which was greater than 50% of the positive cutoff value.

B. TRANSFORMED SIGNAL/CUTOFF VALUES FOR ANTIBODIES TO HTLV-I/II

FIGS. 2A, 2B and 2C show histograms of natural logarithm-transformed signal/cutoff values for antibodies to HTLV-I/II. The signal cutoff (S/C) values obtained in the HTLV-I ELISA for serum from 6080 normal blood donors (top panel), 72 individuals documented to be the HTLV-I+ by DNA analyses (middle panel), and 28 patients with LGL leukemia (bottom panel) were transformed into their natural logarithms (LN) and plotted in histogram form according to the categories presented in Table 2.

TABLE 2

| Category | LN (S/C) Value | Category | LN (S/C) Value |
|---|---|---|---|
| 1 | <−7.01 | 11 | −2.5 to −2.01 |
| 2 | −7.0 to −6.51 | 12 | −2.0 to −1.51 |
| 3 | −6.5 to −6.01 | 13 | −1.5 to −1.01 |
| 4 | −6.0 to −5.51 | 14 | −1.0 to −0.51 |
| 5 | −5.5 to −5.01 | 15 | −0.5 to −0.01 |
| 6 | −5.0 to −4.51 | 16 | 0.0 to 0.49 |
| 7 | −4.5 to −4.01 | 17 | 0.50 to 0.99 |
| 8 | −4.0 to −3.51 | 18 | 1.0 to 1.49 |
| 9 | −3.5 to −3.01 | 19 | 1.5 to 1.99 |
| 10 | −3.0 to −2.51 | 20 | 2.0 to 2.5 |

Categories 16–20 represent positive test values above the cutoff; test values which were negative but greater than 50% above the cutoff value fall within categories 14 and 15.

For purposes of statistical analyses, a two-by-two table was constructed containing the number of normal donors and the number of LGL leukemia patients in categories 1–10 (normal: 4170; LGL leukemia: 0) compared to those in categories 11–20 (normal: 1910; LGL leukemia: 28).

Fisher's exact T-test showed that distribution of ELISA reactivity in LGL sera was different than results obtained in normal sera ($p \leq 1 \times 10^{-8}$). Chi square analyses comparing % of normal sera to % of LGL leukemia sera falling within each category also give similar results ($p \leq 1 \times 10^{-8}$).

The ELISA readings for the LGL leukemia sera clustered around the positive cutoff value, a distribution which was significantly different from the results obtained when testing over 6,000 volunteer blood donor sera, $p \leq 1 \times 10^{-8}$ (FIGS. 2A–2C). None of the control acute or chronic myeloid or lymphoid leukemia patient samples scored positive in this assay. Furthermore, the distribution of their S/C ratio did not differ from that of the volunteer blood donors.

Example 2

PROTEIN BLOT ANALYSIS

Only serum from patient 24 met the Public Health Service criteria for HTLV-I/II seropositivity, with a positive-screening ELISA (Coulter) and antibodies reactive to both gag p24 and env gp46 on Western blots. Differentiation between HTLV-I and HTLV-II was shown using a modified recombinant Western blot assay (Materials and Methods), in which serum from patient 24 reacted to HTLV-II env gp46 (FIG. 3).

Figure 3:
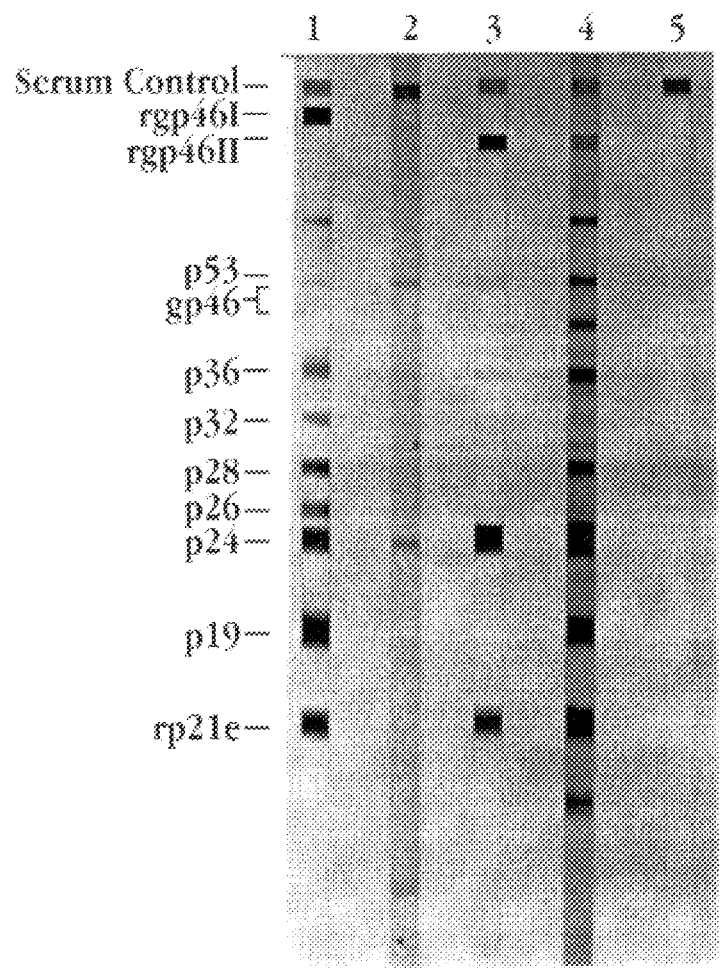
FIG. 3 presents a computer-scanned image of a modified recombinant Western blot assay using control and patient sera.

In FIG. 3, lane 1, HTLV-I seropositive control; lane 2, serum from patient 11 with LGL leukemia; lane 3, HTLV-II seropositive control; lane 4, serum from patient 24 with LGL leukemia; lane 5, seronegative control.

Serum from patient 11 was also positive in the modified Western blot assay showing reactivity to gag p24 and HTLV-I env gp46 (FIG. 3); however, serum from this patient was negative in the whole virus ELISA.

Sera from most patients (25/28, 89%) showed indeterminate reactivity in Western blot assays. In general, reactivity was directed at gag p24 rather than gag p19. These sera did not react to either recombinant HTLV-I or HTLV-II env gp46. However, ten of these indeterminate sera (48%) did react with env p21e, using the Cambridge Western blot assay. Seven of these patients had rheumatoid arthritis. Furthermore, 10 of these sera (40%) reacted with both gag p24 and env p21e using this assay.

Example 3

AMPLIFICATION OF HTLV-I/II SEQUENCES

Genomic DNA samples from the twenty eight LGL leukemia patients were screened for HTLV-I and HTLV-II nucleic acids using the polymerase chain amplification reaction and selected HTLV-I/II specific primers (Materials and Methods).

HTLV-II pol and pX gene regions from bone marrow DNA of patient 24 after PCR amplification were cloned and sequenced (Loughran, et al., 1992). PCR amplification of DNA from the other patients was aimed at detecting these gene sequences, which are highly conserved amongst HTLV-I and HTLV-II isolates (Erlich, et al., 1989).

No such sequences were detected in DNA from any of the other 27 patients tested, including patients whose sera had serologic reactivity to gag p24 and env p21e.

More extensive PCR analyses performed in a limited number of patient samples (8) were also negative for two additional HTLV-I pol gene regions, an HTLV-I env gene region, an HTLV-II gag gene region, and an HTLV-II env gene region. In addition, amplification using primers from other regions of the HTLV I and II genomes and the patients' genomic DNA samples, also gave negative amplification results.

Example 4

FAMILIAL OCCURRENCE OF LGL LEUKEMIA

"Atypical" chronic lymphocytic leukemia was diagnosed in J. E. in 1975, when he was 31 years of age. At that time, his white blood cell count (WBC) ranged between 5 to 10,000/µl with a moderate absolute lymphocytosis and neutropenia of 100–500/µl. From 1976 through 1980 he received intermittent treatment with combination chemotherapy with only modest improvement in neutrophil count.

When evaluated in 1985, his WBC was 4000/µl, with an absolute neutrophil count of 1000/µl. Almost all lymphocytes had LGL morphology, the absolute LGL count was 2400/µl (normal=223±99) (Loughran, et al., 1987). Subsequent complete blood counts have remained unchanged.

The patient's mother was told that she had an "abnormal blood count" in 1975 at age 65 at the time of her son's diagnosis. When evaluated in 1990, her WBC was 6300/µl, with an absolute lymphocytosis of 4950/µl, an absolute LGL count of 3000 µl, and an absolute neutrophil count of 1200/µl. Subsequent blood counts have remained stable.

The mother and son were Caucasian and lived in the Pacific Northwest United States.

A. PHENOTYPE ANALYSES

Lymphocyte phenotyping was carried out on blood samples as follows.

The cell surface phenotype of peripheral blood mononuclear cells was determined using an EPIC cytofluorometer (Coulter, Hialeah, Fla.) and a panel of directly phycoerythrin (PE) or fluorescein (FITC)-conjugated monoclonal antibodies (MAb) as previously described (Loughran, et al., 1987).

Table 3 shows the data from two-color analyses demonstrating markedly increased numbers of the characteristic CD3+, CD16+ or CD3+, CD57+ leukemic LGL phenotype in both patients ("Son" and "Mother").

TABLE 3

ONE- AND TWO-COLOR FLOW CYTOMETRY ANALYSES OF PERIPHERAL BLOOD MONONUCLEAR CELLS FROM FAMILIAL LGL LEUKEMIA PATIENTS

| | Mean % Positive Cells | | |
|---|---|---|---|
| Antigen | Son | Mother | Normals* |
| CD3 | 77 | 58 | 74 ± 6 |
| CD4 | 43 | 23 | 47 ± 4 |
| CD8 | 40 | 41 | 25 ± 5 |
| CD16 | 27 | 24 | 9 ± 4 |
| CD57 | 30 | 34 | 13 ± 6 |
| CD3+, CD16+ | 23 | N.D.+ | 1 ± 1 |
| CD3+, CD57+ | N.D. | 28 | 10 ± 4 |
| | Total Number of Positives Cells/ul | | |
| Antigen | Son | Mother | Normals* |
| CD3 | 2310 | 2857 | 1447 ± 325 |
| CD4 | 1290 | 1143 | 910 ± 188 |
| CD8 | 1200 | 2037 | 485 ± 149 |
| CD16 | 840 | 1167 | 174 ± 94 |
| CD57 | 900 | 1694 | 263 ± 131 |
| CD3+, CD16+ | 690 | N.D. | 25 ± 28 |
| CD3+, CD57+ | N.D. | 1366 | 204 ± 99 |

B. BLOT HYBRIDIZATION ANALYSIS

Genomic DNA of PBMC was studied for T cell receptor gene rearrangement essentially as previously described (Loughran, et al., 1988a). PBMC were isolated by standard methods utilizing "FICOLL-HYPAQUE" density gradient centrifugation (Fan, at al., 1992).

Figure 4:
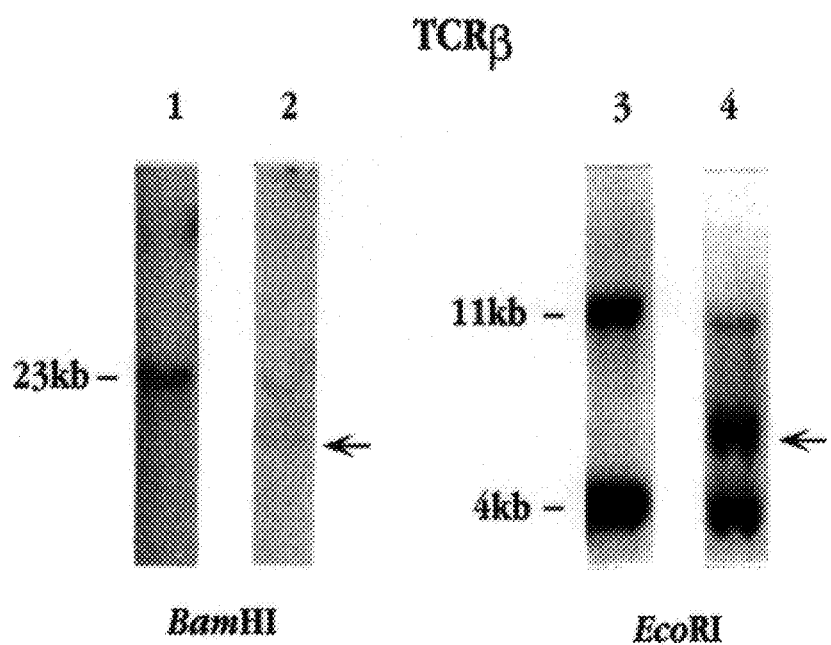
FIG. 4 is a computer-scanned image of a genomic DNA hybridization analysis of genomic DNA isolated from PBMC (LGL-leukemia patients) probed using a radioactively labeled TCRβ gene probe.

Genomic DNA hybridization analysis (Southern analysis) was carried out following standard procedures (Ausubel, et al.). Briefly, genomic DNA was isolated from PBMC and digested with BamHI or EcoRI. The resulting fragments were size-fractionated electrophoretically in a 1.2% agarose gel. DNA was transferred from agarose gels to nylon membranes. The DNA fragments on the membranes were probed using a radioactively labeled TCRβ gene probe (Yoshikai, et al.). The membrane was washed and exposed to X-ray film. A typical autoradiogram is presented in FIG. 4.

In the figure, lanes 1 and 3 represent the germline pattern when analyzing DNA extracted from K562 cell line; lane 2 contains DNA from the patient's mother; and lane 4 contains DNA from the patient, J. E. Arrows indicate the position of rearranged bands. K562 (American Type Culture Collection, 12301 Parklawn Dr., Rockville Md. 20852) is a leukemic cell line and is used as a germline control for non-rearranged T-cell receptor genes.

The results demonstrate the clonal rearrangement of TCRβ gene in DNA extracted from both mother and son.

C. SEROLOGIC ANALYSES

Serum from the son reacted to HTLV-I/II gag proteins p19, p24 and p28, using a modified recombinant Western blot assay (Cambridge Biotech). Reactivity to recombinant HTLV-I/II envelope protein p21e was not observed. Serum from the mother was negative in this assay.

Serum from son and mother tested negative for both HTLV-I and HTLV-II using the "SELECT-HTLV" (Coulter) ELISA.

D. PCR ANALYSES

Gene sequences shared by HTLV-I and HTLV-II (pX and pol) were not detected in either patient; similarly analyses for HTLV-I gag p24 and HTLV-II gag p19 were also negative. Sensitivity of detection was 1–10 copies of HTLV-I or HTLV-II in each assay.

Example 5

LGL LEUKEMIA PATIENT PBMC CO-CULTIVATION WITH HOS CELLS

A. TRANSMISSION OF INFECTIVE RETROVIRUS FROM A PATIENT WITH LGL LEUKEMIA

An IL-2-dependent cell line was obtained from splenic mononuclear cells of a seroindeterminate patient with rheumatoid arthritis and LGL leukemia (Patient 6), and was co-cultured (Clapham, et al., 1983) with a human osteosarcoma cell line (HOS; American Type Culture Collection, 12301 Parklawn Dr., Rockville Md. 20852). The HOS cell line can be productively infected with HTLV-I/II (Clapham, et al., 1983). The cell line resulting from the co-cultivation was designated B-HOS.

Reverse transcriptase (RT) assays were performed at various intervals of cocultivation (Poiesz, et al., 1980). No RT activity was noted in control HOS supernatants, there was minimally elevated RT activity (twofold about background) in LGL leukemia cell line supernatants. However, RT activity was demonstrated in supernatants of B-HOS co-cultivated cell lines.

Continued passage of B-HOS cells with 5-Iodo-2'deoxyuridine (IdUr) resulted in reinduction of RT activity (Table 4). Levels of RT activity observed in B-HOS supernatants were comparable to those obtained from supernatants of MT-2 cell line, a known HTLV-I producer (Miyoshi, et al., 1981).

TABLE 4

REVERSE TRANSCRIPTASE ACTIVITY OF CELL-FREE SUPERNATANTS FROM B-HOS CELL LINE

| | RT Activity (cpm) | | |
|---|---|---|---|
| Supernatant | Background | Sample | Increase Above Background |
| HOS cell line | 17,705 | 15,680 | 0 fold |
| Leukemic LGL cell line | 17,705 | 29,538 | 1.7 fold |
| B-Hos cell line | | | |
| 3 weeks | 17,705 | 46,044 | 2.6 fold |
| 8 weeks | 39,422 | 260,790 | 6.6 fold |
| 11 weeks | 39,020 | 21,354 | 0 fold |
| 11 weeks and IdUr+ | 13,256 | 45,454 | 3.4 fold |
| MT-2 cell line | 13,256 | 63,386 | 4.8 fold |

*10 ml of cell-free supernatant were centrifuged and reverse transcriptase (RT) activity of viral pellets determined using a viral RNA-directed DNA polymerase assay as described (Poiesz, et al., 1980).
+B-HOS cells were treated with IdUr at 20 µg/ml for 18 hours; supernatant from B-HOS was then examined for RT activity 72 hours later.

Further evidence for retroviral protein expression was obtained using commercially available monoclonal antibodies (Mab's) that are immunoreactive with HTLV-I gag proteins p19 and p24 (Robert-Guroff, et al., 1981) (Dupont, Wilmington, Del.). These Mab will also cross-react with HTLV-II-infected cells.

B-HOS cell cultures were screened at various time points for proteins immunoreactive with the monoclonal antibodies. At a time when RT activity was low, there was no cytoplasmic expression of HTLV-I/II gag proteins p19 or p24 by the B-HOS cells.

However, the data presented in FIG. 6 demonstrate that there was an induction of cytoplasmic p19. FIG. 6 shows staining of B-HOS cells with HTLV-I/II anti-p19 monoclonal antibody. B-HOS cells were treated with 60 μg/ml of IdUr for 18 hours, then washed, and examined for p19 expression 24 hours later.

Expression of p19 was evaluated as follows. After fixation in methanol, B-HOS cells were labeled with HTLV-I/II anti-p19 Mab (Dupont, Wilmington, Del.), washed. FITC conjugated F(ab)$_2$, anti-mouse Ig was added as secondary reagent.

Stained cells were examined by flow cytometry. Control cells were stained with IgG$_1$ control antibody (represented by the nonshaded curve in FIG. 6). Cells stained with anti-p19 monoclonal antibody are represented in FIG. 6 by the shaded curve.

Further, there was an induction of cytoplasmic p24 expression by the B-HOS cells after treatment with IdUr (Table 5).

TABLE 5

CYTOPLASMIC EXPRESSION OF HTLV-I GAG ANTIGENS

| Cells | Reactivity with Monoclonal Antibody (% Positive) | |
|---|---|---|
| | Anti-p19 | Anti-p24 |
| Normal T cells | 0 | 0 |
| Leukemic LGL | 0 | 0 |
| HOS | 0 | 0 |
| B-HOS* | 0 | 0 |
| B-HOS induced with IdUr | 31 | 19 |
| MT-2+ | 89 | 91 |

*B-HOS cells were treated with 60 μg/ml of 5-iododeoxyuridine (IdUr) for 18 hours, then washed, and examined for p19 and p24 expression 24 hours later.
+MT-2 is an HTLV-I positive cell line, as control.

B. SUCROSE GRADIENT COMPOSITION

Viral particles were purified from cell culture supernatants by double banding using sucrose gradient centrifugation, as described (Poiesz, et al., 1980). In brief, supernatants from the B-HOS cell line were clarified and viral particles banded on a 22%–65% discontinuous sucrose gradient. The banded pellet was then resuspended in TNE buffer and banded again on a 22–65% continuous sucrose gradient.

Fractions from the gradient were collected and density determined by refractometry. Reverse transcriptase assays were then performed on aliquots from each fraction, as described (Poiesz, et al., 1980). Reverse transcriptase activity using poly (A)·dT$_{12-18}$ and/or (C)·dG$_{12-18}$ peaked in two areas of the gradient, at densities of 1.19 to 1.21 g/ml and 1.10 g/ml. The peak of activities occur in density fractions typical for retroviral particles.

C. ELECTRON MICROGRAPH

B-HOS cells were pelleted and prepared for electron microscopic examination essentially as previously described in Poiesz, et al. (1980). A representative photographs of viral particles are shown in FIGS. 5A and 5B.

In the figure, thin-section electron micrograph of an extracellular viral particle (FIG. 5A) and a particle budding from B-HOS cell line (FIG. 5B), as seen in pelleted B-HOS cells.

Mature extracellular viral particles are approximately 100 nm in diameter, have an electron-dense, centrally located nucleoid surrounded by an outer membrane separated by an electron-lucent area.

The results presented above strongly support a non-prototypical HTLV-I/II retroviral infection associated with LGL leukemia.

Example 6

ISOLATION OF LGL LEUKEMIA-ASSOCIATED VIRUS NUCLEIC ACID SEQUENCES

Genomic DNA was isolated from the PBMC from Patient 6 and from bone marrow of Patient 18. In addition, the genomic DNA of HOS cells co-cultured with a splenic cell line from patient 6 (B-HOS cells, Example 5) was isolated.

Amplification primers were selected based on conserved sequences from the pX and pol gene coding sequences from Bovine Leukemia Virus (BLV; Sherman, et al., 1992; complete BLV sequence, Sagata, et al., 1985). The sequences of these primers are as follows: pX, forward primer SEQ ID NO:1, reverse primer SEQ ID NO:2,—predicted amplified fragment size approximately 113 base pairs, pX specific probe, SEQ ID NO:3; pol, forward primer SEQ ID NO:4, reverse primer SEQ ID NO:5—predicted amplified fragment size 158 base pairs, pol specific probe, SEQ ID NO:6.

Amplification conditions were essentially as previously described (Loughran, et al., 1992).

The amplification products were size fractionated on 1.2% agarose gels. DNA corresponding in size to the predicted fragments for each amplification reaction were isolated from the gel, purified and sequenced.

The sequences of the amplified pX products are presented in FIG. 7 (Patient 6, SEQ ID NO:22; B-HOS, SEQ ID NO:23; Patient 18, SEQ ID NO:24). The sequence of an amplified pol product from the Patient 6 nucleic acid source is presented in FIG. 8 (SEQ ID NO:27). The isolated sequences have been cloned into the "pCRII" cloning vector ("TA CLONING" kit; Invitrogen, San Diego, Calif.).

In FIGS. 7 and 8, the sequences are compared to the following known isolates of Bovine Leukemia Virus: Lambdablv1 (SEQ ID NO:25), Japanese BLV (SEQ ID NO:20); and Pblv1 (SEQ ID NO:26), Belgian BLV (SEQ ID NO:21).

While the invention has been described with reference to specific methods and embodiments, it will be appreciated that various modifications and changes may be made without departing from the invention.

It is claimed:

1. A human osteosarcoma (HOS) cell line infected with a large granular lymphocyte (LGL) leukemia-associated retrovirus.

2. The cell line of claim 1, wherein said cell line is the B-HOS cell line.

3. The cell line of claim 1, wherein infection by said LGL retrovirus is characterized by retroviral transcriptase activity greater than twofold above background.

4. An isolated cell from the cell line of claim 1.

5. A human tissue culture cell line infected with a large granular lymphocyte (LGL) leukemia-associated retrovirus, wherein infection by said LGL retrovirus is characterized by retroviral transcriptase activity greater than twofold above background.

6. The cell line of claim 5, wherein said cell line is a human osteosarcoma (HOS) cell line.

7. An isolated cell from the cell line of claim 5.

8. The cell line of claim 6, wherein said cell line is the B-HOS cell line.

* * * * *

UNITED STATES PATENT AND TRADEMARK OFFICE
CERTIFICATE OF CORRECTION

PATENT NO. : 5,891,723
DATED : April 6, 1999
INVENTOR(S) : Thomas P. Loughran, Jr., et al.

It is certified that error appears in the above-indentified patent and that said Letters Patent is hereby corrected as shown below:

On the title page, item [63]

Under "Related U.S. Application Data," the patent number of parent Ser. No. 08/242,680 should be --5,521,083--.

In column 1, line 8, "NO1 HB 67021" should be --N01 HB 67021-- (replacing a capital O with zero).

Signed and Sealed this

Twenty-third Day of November, 1999

Attest:

Q. TODD DICKINSON

*Attesting Officer*   *Acting Commissioner of Patents and Trademarks*